| United States Patent [19] | [11] | 4,423,055 |
|---|---|---|
| McCombie | [45] | Dec. 27, 1983 |

[54] 6-SUBSTITUTED-HYDROCARBON-2-(SUBSTITUTED-THIO)PENEM-3-CARBOXYLIC ACIDS

[75] Inventor: Stuart W. McCombie, West Orange, N.J.

[73] Assignee: Schering Corporation, Kenilworth, N.J.

[21] Appl. No.: 324,317

[22] Filed: Nov. 23, 1981

Related U.S. Application Data

[63] Continuation-in-part of Ser. No. 62,875, Aug. 1, 1979, abandoned, which is a continuation-in-part of Ser. No. 2,471, Jan. 10, 1979, abandoned, and Ser. No. 91,610, Nov. 5, 1979, abandoned.

[51] Int. Cl.³ .................. C07D 499/00; A61K 31/425
[52] U.S. Cl. ............................ 424/270; 260/245.2 R
[58] Field of Search ................. 260/245.2 R; 424/270, 424/271

[56] References Cited

U.S. PATENT DOCUMENTS 4,168,314 9/1979 Christensen et al. ........ 260/245.2 R
4,282,150 8/1981 Menard ........................ 260/245.2 R
4,283,531 8/1981 Ganguly et al. ............. 260/245.2 R

*Primary Examiner*—Nicholas S. Rizzo
*Attorney, Agent, or Firm*—Gerald S. Rosen; Bruce M. Eisen; Mary S. King

[57] ABSTRACT

6-Substituted-hydrocarbon-2-(substituted-thio)penem-3-carboxylic acids and congeners having useful antibacterial activity are disclosed. The compounds are prepared in a reaction sequence starting with a 4-acyloxy-2-azetidinone.

16 Claims, No Drawings

6-SUBSTITUTED-HYDROCARBON-2-(SUBSTITUTED-THIO)PENEM-3-CARBOXYLIC ACIDS

This application is a continuation-in-part of copending U.S. Ser. No. 062,875, filed Aug. 1, 1979 now abandoned, in turn a continuation-in-part of U.S. Ser. No. 002,471, filed Jan. 10, 1979 now abandoned, and of co-pending U.S. Ser. No. 091,610, filed Nov. 5, 1979 now abandoned, the disclosure of which is incorporated herein by reference.

The present invention relates to 6-substituted-hydrocarbon-2-(substituted-thio)penem-3-carboxylic acids and congeners. More particularly, this invention relates to compounds of the formula

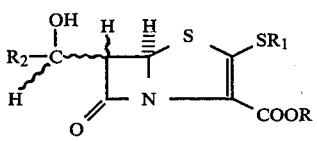

wherein R is hydrogen, an alkali metal cation, or a metabolisable ester group. $R_1$ is lower alkyl, aralkyl, amino(lower)alkyl, mono- or di-(lower)alkylamino(lower)alkyl, carboxy(lower)alkyl, acylamino(lower)alkyl, hydroxy(lower)alkyl, hydroxyaralkyl, alkoxycarbonyl(lower)alkyl, or heteroaralkyl; and $R_2$ is aryl, aralkyl, heteroaryl, heteraralkyl, or hydroxyaralkyl.

The "penems" of this invention are named by reference to the following formula:

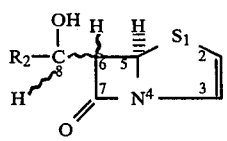

The lower alkyl groups referred to about contain 1 to 6 carbon atoms and are exemplified by methyl, ethyl, propyl, butyl, pentyl, hexyl, and the corresponding branched-chain isomers thereof.

The alkali metal cations referred to above preferably are potassium and sodium but may also be lithium, rubidium, or cesium.

The acyl substituents referred to above contain 2 to 7 carbon atoms and are exemplified by acetyl, propionyl, butyryl, The alkali metal cations referred to above preferably are potassium and sodium but may also be lithium, rubidum or cesium.

The acyl substituents referred to above contain 2 to 7 carbon atoms and are exemplified by acetyl, propionyl, butyryl, valeryl and the like and which may be optionally substituted by up to three chlorine atoms.

The term "aryl" as used herein refers to phenyl substituted by lower alkyl, lower alkoxy and halogen groups, e.g., p-tolyl, o-tolyl, m-tolyl, p-chlorophenyl, o-methoxyphenyl, etc.

The term "heteroaralkyl" as used herein refers to lower alkyl groups substituted by a heteroaryl group such as pyridyl, furanyl, thienyl or the like. The heteroaryl group may optionally contain 1 to 3 lower alkyl substituents, e.g., 2-methylpyridyl, 3-methylthienyl, etc.

The lower alkoxy groups referred to above likewise contain 1 to 6 carbon atoms and are exemplified by methoxy, ethoxy, propoxy, and the like.

The term "aralkyl" denotes lower alkyl groups substituted by one or more aryl groups such as benzyl, phenethyl, benzhydryl and the like.

The term "metabolisable ester" group denotes an ester group which is metabolically removed in the body. Two particularly useful metabolisable ester groups are the phthalidyl group and the pivaloyloxymethyl group.

The foregoing compounds possess several centers of chirality and are produced by the various processes as various isomeric mixtures. The present invention is intended to encompass all isomeric forms of the compounds of formula I, and mixtures thereof.

With respect to those in the penem nucleus itself, the preferred configuration about each center corresponds to that of thienamycin. That is, the carbon atoms at the 5 and 6 positions are of the absolute stereochemistry R and S, respectively. The two hydrogen atoms attached to the 5 and 6 carbon atoms are thus trans to one another. The stereochemistry of the C-8 carbon atom may be either R or S depending on the exact nature of the $R_2$ substituent. For instance, the compounds wherein $R_2$ is methyl preferably have the 8R stereochemistry. The most preferred stereochemical configuration for a compound of this invention wherein $R_2$ is methyl is designated 5R,6S,8R and has the following representative spatial configuration:

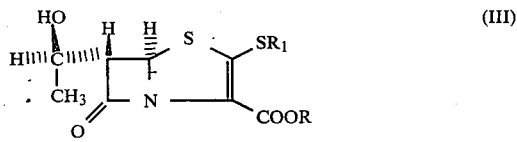

The preferred stereochemical configuration of all the compounds of formula I is that shown in formula III; however, the nomenclature may differ depending on the nature of the $R_2$ substituent. Wherein the $R_2$ group of formula I has a higher priority in the Cahn-Ingold-Prelog system, e.g., a 2-pyridyl group, a compound having the most preferred stereochemical configuration will be designated 5R, 6S, 8S, but be of the same relative spatial configuration at C-5, C-6 and C-8 as the 5R, 6S, 8R compound of formula III.

Certain of the processes of this invention produce these compounds as their racemic mixtures, e.g., 5R,6S,8R compound is produced with its enantiomer (mirror image) i.e., a 5S, 6R, 8S compound, in equal amounts when the starting compound is a racemic mixture. The two enantiomers may be separated by conventional means, e.g., by resolution by fractional crystallizations of optically active salt forms, e.g., the salts derived from optically active amino acids, (−)-brucine, or (+)- and (−)-ephedrine. Preferably, the chiral compounds of formula I are produced in their pure enantiomeric form by utilizing optically active intermediates in the synthetic procedure. These optically active intermediates may be produced by conventional resolution or by stereospecific synthesis according to the procedures of Girijavallabhan et al., U.S. Ser. No. 091,609, filed Nov. 5, 1979 and now abandoned, entitled "SYNTHESIS OF OPTICALLY ACTIVE INTERMEDIATES FOR PENEM SYNTHESIS", and described in E.P.O. Published Application No. 0013662, the disclosures of both of which are incorporated herein by reference. A preferred method of preparing the compounds of formula I, specifically described in Example 16, utilizes procedures of Adriano Afonso and Frank Hon, U.S. Pat. No. 4,347,183 (of common assignee as the instant application), the disclosure of which is incorporated herein by reference.

These designations of absolute spatial configuration are based on X-ray crystal analysis.

Preferred compounds of formula I are those wherein $R_2$ is a lower alkyl group. Particularly preferred are those compounds of formula I wherein $R_2$ is a methyl group.

A most particularly preferred group of compounds of formula I encompassed by this invention are those wherein $R_2$ is methyl, $R_1$ is lower alkyl and the stereochemical configuration is 5R, 6S, 8R.

The compounds of this invention possess antibacterial activity of both the gram-positive and gram-negative type. Thus, when tested in standardized microbiological assays, the compounds of this invention are active against such gram-positive organisms as *Staphylococcus epidermidis*, and *Bacillus subtilis*, and such gram-negative organisms as *E. coli* and Salmonella at test levels of 0.1 to 100 μg/ml. Additionally, they show activity against such organisms in the presence of penicillanase indicating a resistance to this enzyme and are inhibitors of beta-lactamases. For instance, potassium (5R,6S,8R)-6-(1-hydroxy-ethyl)-2-ethylthiopenem-3-carboxylate in equal admixture with its 5S,6R,8S enantiomer is active against *Staphylococcus epidermidis* 0701603 (also identified as "7670103") at a test level of 1 μg/ml and against *E. coli* JR66 at a test level of 1 μg/ml. When tested against *B. subtilis* 1119601 (a beta-lactamase-containing organism), this compound exhibits activity at 0.125 μg/ml. The preferred pure enantiomer, i.e., potassium (5R,8S,8R)-6-(1-hydroxyethyl)-2-ethylthiopenem-3-carboxylate is active against *Staphylococcus epidermidis* 0701603 at a test level of less than 0.06 μg/ml and against *E. coli* JR66 at a test level of 0.5 μg/ml, and against *B. Sublilis* at a test level of 0.06 μg/ml.

Thus, the present invention includes within its scope pharmaceutical compositions comprising an antibacterially effective amount of a penem of formula I together with a compatible, pharmaceutically acceptable carrier or coating. Also included within this invention is the method of eliciting an antibacterial response in a warm-blooded animal having a susceptible bacterial infection which comprises administering to said animal a non-toxic, antibacterially effective amount of a compound of formula I.

The dosage administered of the penems of this invention is dependent upon the age and weight of the animal species being treated, the mode of administration, and the type and severity of bacterial infection being prevented or reduced. Typically, the dosage administered per day will be in the range of 100–5000 mg, with 500–1000 mg being preferred.

For oral administration, the compounds of this invention may be formulated in the form of tablets, capsules, elixirs or the like. Likewise, they may be admixed with animal feed. They may also be applied topically in the form of ointments, both hydrophilic and hydrophobic, in the form of lotions which may be aqueous, non-aqueous or of the emulsion type, or in the form of creams.

The compounds of formula I may be utilized in liquid form such as solutions, suspensions and the like for otic and optic use and may also be administered parenterally via intramuscular injection.

The compounds of this invention are preparable by a reaction sequence starting with 4-ethylthioazetidin-2-one (preparable according to the procedures of *Liebigs Ann. Chem.*, 1974, 539–560). This starting material is treated with a suitable amine-protecting group (for the NH function) to afford the 1-protected-4-ethylthioazetidin-2-one. Preferred protecting groups are those such as t-butyldimethylsilyl, triethylsilyl, or tetrahydropyranyl, with t-butyldimethylsilyl being particularly preferred. Typically, the reaction is conducted in an organic solvent such as dichloromethane or chloroform in the presence of an acid acceptor. The acid acceptor may be an inorganic or organic base, but organic bases such as triethylamine are generally preferred. Typically, temperatures are from 0° C. to room temperature, and typical times range from 5–60 minutes, depending upon the nature of the reactants.

The 1-protected-4-ethylthioazetidin-2-one is treated with a strong base to form an anion at the 3-position which is reacted without isolation with an aldehyde of the formula IV

wherein $R_2$ is as hereinbefore defined; to afford the intermediate of the formula V:

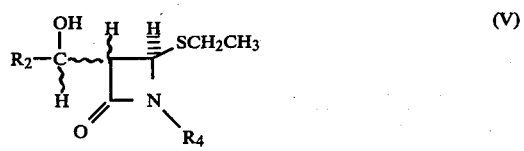

wherein $R_2$ is as hereinbefore defined and $R_4$ is a nitrogen-protecting group. The base utilized to form the anion is one such as lithium di-isopropylamide, lithium bis(trimethylsilyl)amide, n-butyl lithium or sec-butyl lithium. Generally, an anhydrous aprotic solvent such as tetrahydrofuran or ethyl ether is utilized. Preferred temperatures range from −80° to −60° C. during the production of the anion. After addition of the aldehyde of formula IV, the reaction mixture may be allowed to warm to room temperatures. This reaction produces a mixture of 4 isomers which may be utilized further without separation or which may be optionally separated by chromatography at this stage.

The intermediate of formula V is then treated with a suitable hydroxy-blocking reagent to afford the intermediate of the formula VI:

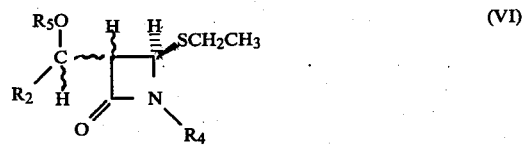

wherein $R_2$ and $R_4$ are as hereinbefore defined and $R_5$ is a suitable hydroxy protecting group. Suitable hydroxy protecting groups are those such as 2,2,2-trichloroethoxycarbonyl, 1,1,1-trichloro-2-methyl-2-propoxycarbonyl, p-nitrobenzyloxycarbonyl or allyloxycarbonyl, with 2,2,2-trichloroethoxycarbonyl being preferred. Typically, the reaction is conducted in an organic solvent, e.g., methylene chloride in the presence of an acid acceptor, e.g., triethylamine.

The R₄-nitrogen-protecting group may then be removed by conventional methods depending upon the exact nature of the R₄ nitrogen protecting group utilized. This affords the intermediate of the formula VII

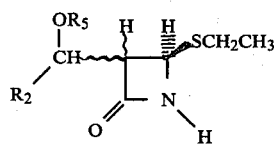

(VII)

wherein R₂ and R₅ are as hereinbefore defined.

Alternatively, the R₄ protecting group V may be first removed to afford the intermediate of the formula VIII

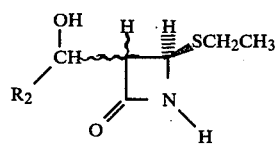

(VIII)

followed by introduction of the hydroxy-protecting group to give VII.

The intermediate of formula VII is then treated with chlorine, followed immediately by a nucleophile of the formula IX

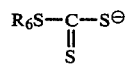

(IX)

wherein R₆ is lower alkyl, mono- or di-loweralkylamino(lower)alkyl or acylamino(lower)alkyl, aralkyl, heteroaralkyl, lower alkoxycarbonyl(lower)alkyl, or R₇-amino(lower)alkyl, R₅-hydroxy(lower)alkyl, R₅-hydroxyaralkyl or R₈-carboxy(lower)alkyl wherein R₅ is as hereinbefore defined and the R₇ is a suitable protecting group on the amino function, and R₈ is a suitable protecting group on the carboxy function, affords predominately the trans compounds of formula X, i.e., compounds of the formula Xa:

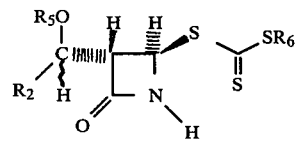

(Xa)

wherein R₂, R₅ and R₆ are as hereinbefore defined.

The nucleophile of formula IX is generated in situ by reaction of carbon disulfide, the appropriate thiol and a base such as potassium or sodium hydroxide. Generally, the addition of chlorine is at low temperatures (−30° to −10° C.), but the subsequent reaction with the nucleophile of formula IX is conducted at slightly higher temperatures, e.g., −10° to +10° C. This reaction produces predominately the two trans isomers, e.g., the compounds differing in their relative stereochemistry at the asymmetric carbon attached at the 3-position of the azetidin-2-one ring. These two isomers are separated by conventional methods, e.g., crystallization and/or chromatography, at this stage of the reaction sequence.

In the foregoing procedure, if the removal of the R₄-nitrogen-protecting group and introduction of the R₅-oxygen-protecting group is postponed until after the reaction with chlorine and the nucleophile of formula IX, there is produced in a product mixture containing predominately the two cis isomers of the formula Xb after appropriate introduction of the R₅ hydroxy-protecting group

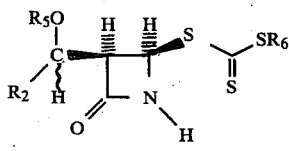

(Xb)

wherein R₂, R₃ and R₆ are as hereinbefore defined, which are then separated by conventional methods, e.g., crystallization and/or chromatography, at this stage of the reaction sequence, together with the two trans isomers.

The compounds of formula Xa and Xb are each produced by the above-described processes in admixture with an equal quantity of their mirror images. Where the pure optically active final products are described, the intermediates of formula Xa and Xb may be resolved by conventional means into their optically active forms or produced by the aforementioned stereospecific synthetic procedure of Girijavallabhan et al., also described in E.P.O. Published Application No. 0013662. When the pure optically active forms of the compounds of formula Xa and Xb are utilized in the following synthetic procedure, the corresponding pure optically active penem is produced.

The nitrogen of the lactam of formula X is then reacted with an ester of glyoxylic acid to afford the compound of formula XI:

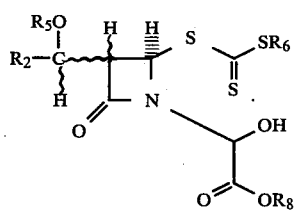

(XI)

wherein R₂, R₅ and R₆ are as hereinbefore defined, and R₈ is a carboxy protecting group such as p-nitrobenzyl, benzyl, allyl or benzhydryl.

In a highly preferred embodiment, R₈ will be an allyl group so as to provide the intermediates of the formula:

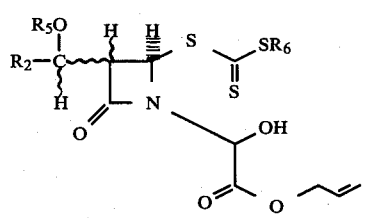

(XIa)

wherein R₂, R₅ and R₆ are as hereinbefore defined. This reaction is usually preferably conducted at reflux temperatures in a non-polar aprotic solvent such as tetrahydrofuran or benzene. Reaction times of 2–10 hours are generally typical.

The compound of formula XI is then treated with a chlorinating or brominating agent, e.g., thionyl chloride, methanesulfonyl chloride, thionyl bromide, or phosphorus tribromide, in the presence of an equivalent of an acid acceptor, e.g., pyridine or triethylamine, so as to afford replacement of the hydroxy group in the 1-glyoxylate function so as to produce the compound of formula XII:

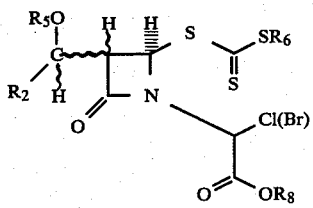
(XII)

wherein $R_2$, $R_5$, $R_6$ and $R_8$ are as hereinbefore defined. Suitable solvents are those such as methylene chloride, tetrahydrofuran or benzene. Temperatures of about 0°–20° C. and reaction times of 10–60 minutes are generally preferred.

The chloride or bromide of formula XII is then reacted with a suitable phosphine, e.g., tri-p-methoxyphenyl phosphine, tributylphosphine or most preferably, triphenylphosphine to afford the compound of the formula XIII:

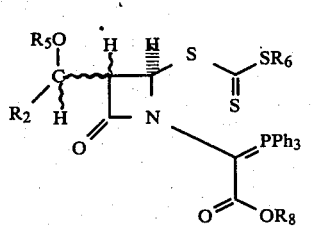
(XIII)

wherein $R_2$, $R_5$, $R_6$ and $R_8$ are as hereinbefore defined. Typically, the reaction is conducted at room temperatures in a polar, aprotic solvent such as hexamethylphosphoramide or dimethylformamide. Reaction times generally vary from about 12–48 hours.

The phosphorane is most preferably isolated and then heated to cause cyclization resulting in the compound of formula XIV:

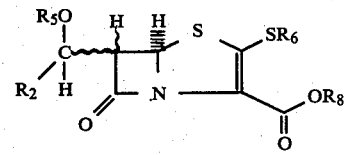
(XIV)

wherein $R_2$, $R_5$, $R_6$ and $R_8$ are as hereinbefore defined. The cyclization is generally conducted at reflux temperatures in an organic solvent such as benzene, toluene or xylene under an inert atmosphere, e.g., nitrogen or argon. Reaction times generally vary from 12–48 hours.

The transformations of compound X to compound XIII is generally according to the procedures described by Woodward, et. al., *Helv. Chim. Acta.*, 55, 408–423 (1972).

At alternate route to the compound of formula XIV to this synthetic procedure involves heating the compound of formula XII with trimethoxyphosphine to give the corresponding dimethoxyphosphonate. Treatment of this phosphonate with a base such as sodium hydride in a polar solvent, e.g., dimethylformamide results in an unisolated intermediate of the structure:

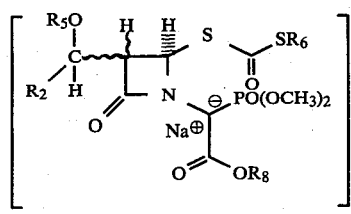

wherein $R_2$, $R_5$, $R_6$ and $R_8$ are as hereinbefore defined, which, upon heating, cyclizes to form the intermediate of formula XIV.

A further alternate involves reaction of the compound of formula XIII with sodium diphenylphosphonate to give an intermediate diphenylphosphonate which, upon treatment with base gives an unisolated intermediate of the formula:

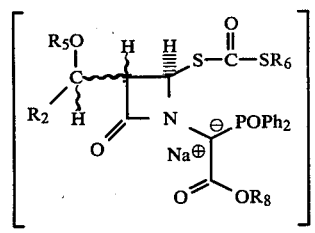

wherein $R_2$, $R_5$, $R_6$ and $R_8$ are as hereinbefore defined. Heating this intermediate also results in the cyclized compound of formula XIV.

Removal of the protecting groups $R_5$, $R_7$ and $R_8$ of the compounds of formula XIV results in the desired product of formula I. The conventional $R_7$ protecting groups, e.g., benzyloxycarbonyl, p-nitrobenzyloxycarbonyl and benzhydryloxycarbonyl, and $R_9$ protecting groups, e.g., benzyl, p-nitrobenzyl and benzhydryl, can be removed by hydrogenation. Certain $R_5$ and $R_7$ protecting groups such as trichloroethoxycarbonyl may be removed prior to the $R_8$ group by deprotection via zinc/acetic acid in a suitable aprotic solvent such as tetrahydrofuran. Most preferably, however, the allyl protecting group will be utilized as $R_8$. This group is most preferably removed by the procedure of McCombie, described in copending U.S. Ser. No. 002,472, filed Jan. 10, 1979, and entitled "Deprotection of Allylic Esters, Carbonates and Carbamates Catalyzed by Palladium Compounds". The McCombie deprotection procedure utilizes a suitable aprotic solvent, such as tetrahydrofuran, diethyl ether or methylene chloride, with potassium or sodium 2-ethylhexanoate or 2-ethylhexanoic acid and a mixture of a palladium compound and triphenyl phosphine as the catalyst. This deprotection method is particularly suitable for the sensitive beta-lactam carboxylates of this invention. Use of the potassium or sodium 2-ethylhexanoate provides the corresponding salt, while use of 2-ethylhexanoic acid affords the free carboxy, amine or hydroxy group.

Compounds preparable by the above reaction schemes include the following representative compounds of this invention each together with its enantiomer when prepared from racemic starting materials, and the pure chiral form when prepared from chiral intermediates.

The most highly preferred stereochemical isomers are named:

potassium (5R,6S,8R)-6-(1-hydroxyethyl)-2-ethylthiopenem-3-carboxylate; potassium (5R,6S,8R)-6-(1-hydroxyethyl)-2-methylthiopenem-3-carboxylate; potassium (5R,6S,8R)-6-(1-hydroxyethyl)-2-benzylthiopenem-3-carboxylate; potassium (5R,6S,8R)-6-(1-hydroxyethyl)-2-p-methylbenzylthiopenem-3-carboxylate; potassium (5R,6S,8R)-6-(1-hydroxyethyl)-2-(3-pyridyl)methylthiopenem-3-carboxylate; sodium (5R,6S,8R)-6-(1-hydroxyethyl)-2-(2-acetylaminoethyl)-thiopenem-3-carboxylate; sodium (5R,6S,8R)-6-(1-hydroxyethyl)-2-p-hydroxybenzyl-3-carboxylate;
(5R,6S,8R)-6-(1-hydroxyethyl)-2-(2-aminoethylthio)-penem-3-carboxylic acid;
(5R,6S,8R)-6-(1-hydroxyethyl)-2-(2-hydroxyethylthio)-penem-3-carboxylic acid,
(5R,6S,8R)-6-(1-hydroxyethyl)-2-(2-carboxyethylthio)-penem-3-carboxylic acid;
(5R,6S,8R)-6-(1-hydroxyethyl)-2-(methoxycarbonylmethylthio)penem-3-carboxylic acid;
(5R,6S,8R)-6-(1-hydroxyethyl)-2-(2-aminoethylthio)-penem-3-carboxylic acid;
(5R,6S,8S)-6-(α-hydroxybenzyl)-2-(2-aminoethylthio)-penem-3-carboxylic acid;
(5R,6S,8R)-6-(1-hydroxyethyl)-2-(2-dimethylaminoethylthio)penem-3-carboxylic acid;
(5R,6S,8R)-6-(1-hydroxyethyl)-2-(2-methylamioethylthio)penem-3-carboxylic acid;
potassium (5R,6S,8S)-6-(α-hydroxybenzyl)-2-methylthiopenem-3-carboxylate;
potassium (5R,6S,8S)-6-[1-hydroxy-1-(4-pyridyl)methyl]-2-methylthiopenem-3-carboxylate;
potassium (5R,6S,8S)-6-(α-hydroxy-p-hydroxybenzyl)-2-methylthiopenem-3-carboxylate;
potassium (5R,6S,8R)-6-(α-hydroxyphenethyl)-2-methylthiopenem-3-carboxylate;
potassium (5R,6S,8S)-6-(α-hydroxy-p-methylbenzyl)-2-ethylthiopenem-3-carboxylate;
(5R,6S,8R)-6-(1-hydroxyethyl)-2-(1-propylthio)penem-3-carboxylic acid;
(5R,6S,8S)-6-(α-hydroxybenzyl)-2-(1-propylthio)-penem-3-carboxylic acid;
(5R,6S,8S)-6-[1-hydroxy-1-(2-thienyl)methyl]penem-3-carboxylic acid;
(5R,6S)-6-(1-hydroxymethyl)-2-ethylthiopenem-3-carboxylate, and
(5R,6R)-6-(1-hydroxymethyl)-2-ethylthiopenem-3-carboxylate.

The following preparations describe in detail the compounds of the present invention and processes for their preparation. It will be apparent to those skilled in the art that many modifications, both of materials and methods, may be practiced without departing from the spirit and scope of the invention.

PREPARATION A

4-Ethylthioazetidin-2-one

Potassium hydroxide (24 g) is dissolved in water (50 ml) and ethanol (300 ml), cooled to 0°–5° C. and ethanethiol (24 g) added, followed by 4-acetoxyazetidin-2-one (43 g). The solution is stirred under nitrogen at room temperature for 20 hours, then added to 10% aqueous sodium chloride solution (1 liter) and extracted four times with 300 ml portions of dichloromethane. The combined extracts are washed twice with saturated sodium chloride, the combined washings back-extracted with an equal volume of dichloromethane, and the combined organic layers dried over anhydrous magnesium sulfate, and evaporated. The residue is dried to constant weight under high vacuum to give the title product as a brown oil, having infrared spectrum $\nu_{max}$ (CH$_2$Cl$_2$ solution) at 3300, 1765 cm$^{-1}$.

PREPARATION B

1-(t-Butyldimethylsilyl)-4-ethylthioazetidin-2-one

A solution of 4-ethylthioazetidin-2-one (43 g) and triethylamine (55 ml) in dichloromethane (300 ml) is stirred at 0°–5° C. and t-butyl(chloro)dimethylsilane (58 g) is added in portions over 5 minutes. The solution is then stirred at room temperature for 0.5 hours. The mixture is washed with 200 ml portions of 0.2 N hydrochloric acid, water and sodium bicarbonate solution, dried and evaporated, and the residue distilled at high vacuum to give a small forerun (e.g., 60°–70° C./0.1 mm), followed by the title product, boiling point 110°–120° C./0.1 mm pressure as a nearly colorless oil, having infrared spectrum $\nu_{max}$ (film) at 1755 cm$^{-1}$.

PREPARATION C

1-(t-Butyldimethylsilyl)-3-(1-hydroxyethyl)-4-ethylthioazetidin-2-one

A solution of lithium di-isopropylamide is prepared by adding 1.6 M butyllithium in hexane (6.7 ml) to diisopropylamine (1.01 g) in tetrahydrofuran (5 ml) at 0° C. under argon. The resulting solution is added slowly to a solution of 1-(t-butyldimethylsilyl)-4-ethylthioazetidin-2-one (2.45 g) in dry tetrahydrofuran (10 ml) at −70° to −80° C. After 5 minutes, freshly distilled acetaldehyde (1 ml) is added, the mixture warmed to 0° C. over 0.5 hour and quenched with acetic acid (1 ml). Dichloromethane (50 ml) is then added, and the solution is washed with water and sodium bicarbonate, dried and evaporated. The residue is dried at high vacuum to give a yellow oil (2.30 g) consisting mainly of the four isomers of the title compound, having infrared spectrum $\nu_{max}$ (CH$_2$Cl$_2$) at 3300 and 1755 cm$^{-1}$.

Chromatography on silica gel, eluting with 10% ether in dichloromethane gave partial separation, with fractions containing pure samples of the least polar component (a cis isomer) and both more polar components (the two trans isomers); one of the latter could be crystallized from ether-hexane; melting point 52°–53° C.

PREPARATION D

1-(t-Butylmethylsilyl)-3-(1-trichloroethoxycarbonyloxyethyl)-4-ethylthioazetidin-2-one A solution of 1-(t-butyldimethylsilyl)-3-(1-hydroxyethyl)-4-ethylthioazetidin-2-one (mainly trans isomers; 7.65 g) and pyridine (4.75 ml) in dichloromethane (100 ml) is stirred, at 0°–5° C., and trichloroethyl chloroformate (6.15 g) is added dropwise. The solution is stirred to room temperature during 1 hour. After washing with 1 N sulfuric acid and water, it is dried and evaporated to give the title compound as a pale yellow oil (11.6 g) which can be used without further purification in Preparation E. A sample partially solidified at −20° C., and two recrystallizations from hexane gave a pure isomer, melting point 92°–93° C., having infrared spectrum $\nu_{max}$ (CH$_2$Cl$_2$) at 1760, 1745 cm$^{-1}$.

PREPARATION E 3-(1-Trichloroethoxycarbonyloxyethyl)-4-ethylthioazetidin-2-one 1-(t-butyldimethylsilyl)-3-(1-trichloroethoxycarbonyloxyethyl)-4-ethylthioazetidin-2-one (11.55 g) in tetrahydrofuran (160 ml) is stirred with water (20 ml) and concentrated hydrochloric acid (20 ml) for 2.5 hours at room temperature, then isolated by addition of dichloromethane (250 ml), followed by washing with 10% aqueous sodium chloride (2×150 ml). The organic phase is then dried and evaporated to the title compound as a yellow oil (6.5 g), having infrared spectrum $\nu_{max}$ (film) at 3400, 1770, 1750 cm$^{-1}$.

PREPARATION F

Ethyl-[trans-(1-Trichloroethoxycarbonyloxyethyl)-2-azetidinon-4-yl]trithiocarbonate The product of Preparation E (6.5 g) is stirred in dichloromethane (100 ml) at −20° C. and a 0.96 M solution of chlorine in carbon tetrachloride (19.4 ml) is added. The resulting solution is added to a rapidly stirred trithiocarbonate solution at 0°–5° C. prepared from ethanethiol (4.2 ml) in ethanol (50 ml) with addition of 1 M aqueous potassium hydroxide (56 ml) followed by carbon disulfide (15 ml). After stirring the mixture at 0°–5° C. for 15 minutes, excess dichloromethane is added and the solution is washed with water and aqueous sodium bicarbonate, dried and evaporated.

The resulting mixture is chromatographed on silica gel (100 g), initially eluting with 10% dichloromethane in hexane to remove the by-product [CH$_3$CH$_2$S S CS SCH$_2$CH$_3$, (diethyl tetrathiopercarbonate), a yellow nonpolar oil], then dichloromethane to give the title compound as an approximately 3:1 isomeric mixture, the major isomer being the less polar on thin layer chromatography in 5% ether-dichloromethane.

The major isomer is crystallized from the mixture using ether/hexane mixtures, affording in 3 crops a product having a melting point of 92°–93° C. and having infrared spectrum $\nu_{max}$ (CH$_2$Cl$_2$) at 3350, 1770 and 1745 cm$^{-1}$ (yellow needles). X-ray crystallography shows this isomer to be the 5R, 6S, 8R isomer.

Chromatography of the final mother liquors on silica gel using 3:1 dichloromethane:hexane gives additional fairly pure major isomer and minor isomer, the latter crystallized with some difficulty from ether-hexane as yellow prisms, melting point 118°–120° C.

PREPARATION G

Ethyl [1-t-butyldimethylsilyl-3-(1-hydroxyethyl)-2-azetidinon-4-yl]trithiocarbonate (isomeric mixture)

1-t-butyldimethylsilyl-3-(1-hydroxyethyl)-4-ethylthio-2-azetidinone (15.0 g of an isomeric mixture prepared in Preparation C) is dissolved in dichloromethane (200 ml) and stirred at −20° C. during addition of chlorine in carbon tetrachloride (53 ml of 1.05 M solution).

A thiocarbonate solution is prepared from potassium hydroxide (8.9 g) in water (30 ml) and ethanol (300 ml) with addition of ethanethiol (12 ml), then carbon disulfide (40 ml). This solution is stirred at 0°–5° C. and the above chlorination mixture added. After 0.5 hours at 0°–5° C., the mixture is extracted with dichloromethane, washing with water and aqueous sodium bicarbonate, dried (MgSO$_4$) and evaporated.

The resulting oil is dissolved in carbon tetrachloride and chromatographed on 300 g silica gel, eluting rapidly with carbon tetrachloride to remove the by-product (CH$_3$CH$_2$S—S—CS—S—CH$_2$CH$_3$), followed by 20% ether—carbon tetrachloride to give the title compound as an isomeric mixture as a yellow oil (15 g). By PMR spectrum, the ratio of cis:trans is determined to be about 2:1.

PREPARATION H

Ethyl [1-butyldimethylsilyl-3-(1-trichloroethoxycarbonyloxyethyl)-2-azetidinon-4-yl]trithiocarbonate Ethyl [1-t-butyldimethylsilyl-3-(1-hydroxyethyl)-2-azetidinon-4-yl]trithiocarbonate (15.0 g) and pyridine (4.3 ml) is stirred in dichloromethane (50 ml) at 0°–5° C. and trichloroethyl chloroformate (7.4 ml) is added dropwise. The mixture is stirred at room temperature for 2 hours, then diluted with dichloromethane, washed with 0.2 N sulfuric acid, water and sodium bicarbonate. After drying over anhydrous magnesium sulfate, it is evaporated to give a mixture. This mixture is then separated by high pressure liquid chromatography (HPLC) on silica gel, using hexane-dichloromethane mixtures as eluting solvent. The first eluted component is a trans isomer (as determined by nuclear magnetic resonance), obtained as an oil. On hydrolysis, it affords the desilylated thiocarbonate, melting point 92°–93° C., corresponding to the major isomer of the title compound of Preparation F. The second eluted component is a cis isomer of the title compound of this example obtained as a yellow oil, $\nu_{max}$ (film) 1750 cm$^{-1}$. The third eluted component is the second cis isomer of the title compound, obtained as a waxy yellow solid, melting point 80°–85° C. The final component is the remaining trans isomer of the title compound, obtained as a yellow oil which on hydrolysis gives the trans desilylylated thiocarbonate, melting point 116°–118° C., corresponding to the minor isomer of Preparation F.

PREPARATION I cis-Ethyl [3-(1-trichloroethoxycarbonyloxyethyl)-2-azetidinon-4-yl]trithiocarbonate (two isomers)

(i) Isomer I

The first eluted cis-N-silyl isomer from the above Preparation H is hydrolyzed by stirring in tetrahydrofuran:water:concentrated hydrochloric acid (20:1:1 by volume) at room temperature until thin layer chromatography (tlc) shows the reaction to be complete. The mixture is extracted in ether:water and the organic phase dried and evaporated. The residue is crystallized from ether:hexane to give yellow needles, melting point 108°–111° C.

(ii) Isomer II

By an identical process starting with the second eluted cis-N-silyl isomer of Preparation H, the corresponding thiocarbonate is obtained from ether:hexane as yellow needles, melting point 118°–120° C.

PREPARATION J

Allyl Glyoxylate Hydrate

Lead tetraacetate (70 g) is added in portions over one half hour to a stirred solution of diallyl tartarate (40 g)

in ethyl acetate (400 ml). The mixture is then stirred for an additional one half hour, filtered and washed with ethyl acetate. The filtrate is treated with 10 ml water and evaporated at 50° C./100 mm pressure to remove the ethyl acetate. This residue is distilled at about 30 mm pressure. After initial removal of acetic acid, the title product is collected at 70°–80° C./30 mm, as a colorless oil.

PREPARATION K

Allyl Oxalyl Chloride

Allyl alcohol (11.6 g.) is added dropwise with stirring to a cold (0° C.) solution of oxalyl chloride (25.4 g.) in dry ether (50 ml.) while maintaining the temperature of the reaction mixture during the addition at 10°–12° C. The reaction mixture is then stirred overnight followed by removal of the solvent in a rotary evaporator. The resultant residue is distilled to yield allyl oxalyl chloride as a colorless liquid (16 g.), b.p. 68°–70° C./44 mm.

PREPARATION L

(3S, 4R, 5R)-Ethyl[3-(1-trichloroethoxycarbonyloxyethyl)-2-azetidinon-4-yl]trithiocarbonate A. To a solution of 100 g 6-β-aminopenicillanic acid in 1200 ml 2.5 N sulfuric acid is added 150 g sodium bromide. To the stirred solution at 0° C. is added simultaneously 40 g sodium nitrite in 150 ml water and 40 ml bromine. The addition is completed in 10 minutes, maintaining the temperature at 0° to 5° C. The mixture is then stirred rapidly for 1 hour, then filtered. The filter cake is washed with water and taken up in 600 ml ethyl acetate. The ethyl acetate solution is washed with water. After drying over anhydrous sodium sulphate, the solvent is removed under vacuum to afford 67 g in 85:15 ratio (by NMR data) of 6,6-dibromopenicillanic acid and 6-β-bromopenicillanic acid.

IR: 728 cm$^{-1}$ and 1800 cm$^{-1}$

NMR: δ=5.7, 1H, s; δ=4.5, 1H, s; δ=1.55–1.67, 6H (CDCl$_3$).

B. To a solution of 67 g in 85.15 ratio of 6,6-dibromopenicillanic acid to 6β-bromopenicillanic acid in 500 ml dimethylformamide at 0° C. is added 37.3 g finely powdered potassium carbonate. The solution is stirred 5–10 minutes and 38.3 g methyl iodide is added. The reaction mixture is then stirred for 2 hours allowing the temperature to come to ambient. The reaction is followed by thin layer chromatography eluting with methylene chloride. When complete, the reaction is decanted and the solvent removed under high vacuum to leave 100 ml of solution. To this is added 600 ml ethyl acetate. The solution is then washed with water, dried over anhydrous sodium sulphate and concentrated under vacuum to afford 63 g crude methyl ester. Subsequently, 48 g of pure methyl 6,6-dibromopenicillanate is isolated from this crude product by high pressure liquid chromotography eluting with methylene chloride.

NMR: δ=5.7, 1H, s; δ=4.48, 1H, s; δ=3.73, 3H, s; δ=1.42, 3H, s; 1.59, 3H, s (CDCl$_3$).

C. To a solution of 13.7 g methyl 6,6-dibromopenicillanate in 250 ml dry tetrahydrofuran at −78° C. under nitrogen is added 14.7 ml of 3 M methyl magnesium bromide in ethyl ether. After stirring for 30 minutes at −78° C., 8 g of freshly distilled acetaldehyde is added and stirring continued for 45 minutes. The reaction mixture is warmed to −20° C. at which time 50 ml 1 M potassium phosphate monobasic is added and stirring continued for 5 minutes. The reaction mixture is then poured into 1 liter cold ethyl acetate and washed once with 150 ml brine solution and twice with 150 ml water. The ethyl acetate layer separated, dried over anhydrous sodium sulfate and evaporated under vacuum. The products, methyl 6α-bromo-6β-(1-hydroxyethyl)-penicillanate and methyl 6β-bromo-6α-(1-hydroxyethyl)penicillanate, are detected by thin layer chromatography on silica gel eluting with 10% ethyl acetate/chloroform.

D. To a solution of 8.0 g methyl 6-bromo-6-(1-hydroxyethyl)penicillanate in 200 ml 95% ethanol is added 800 mg 10% palladium on calcium carbonate. The solution is shaken under 30 lbs hydrogen pressure for 5 hours. Disappearance of starting material is followed by thin layer chromatography eluting with 20% ethyl acetate/chloroform. The catalyst is filtered and 100 ml 1 M potassium phosphate buffer at pH 7 is added. The precipitate formed is filtered and washed with ethanol. The ethanol is removed under vacuum and 200 ml ethyl acetate added. After washing twice with 50 ml water, and drying over anhydrous sodium sulfate, the ethyl acetate is removed under vacuum to afford a crude mixture of methyl 6-(1-hydroxyethyl) penicillanate. Column chromatography of 18.g of said mixture eluting with 20% ethyl acetate affords 6.4 g methyl (5R,6S,8R)-6-(1-hydroxyethyl)-penicillanate.

NMR: δ=2.4–2.7, 1H, d; δ=4.41, 1H, s; δ=3.74, 3H, s; δ=3.2–3.33, 1H; δ=1.25–1.35, 3H, d; δ=1.44, 3H, s; δ=1.61, 3H, s (CDCl$_3$).

E. To a solution of 6.2 g methyl (5R,6S,8R)-6-(1-hydroxyethyl)penicillanate in 60 ml. dry methylene chloride at 0° C. under nitrogen is added 3.8 ml pyridine then 3.3 ml β,β,β-trichloroethylchloroformate. The reaction is stirred 15 minutes until all material is reacted (as determined by thin layer chromatography with 20% ethyl acetate/chloroform). The solution is poured into 250 ml cold methylene chloride and washed twice with cold 10% phosphoric acid solution, once with cold dilute sodium bicarbonate, and then with water. After drying over anhydrous sodium sulfate, the solvent is removed under vacuum to afford 10.0 g methyl (5R,6S,8R)-6-(1-trichloroethoxycarbonyloxyethyl)-penicillanate.

NMR: δ=5.13–5.16, 1H, d; δ=4.78, 2H, s; δ=4.43, 1H, s; δ=3.76, 3H, s; δ=3.38–3.58, 1H; δ=1.45–1.63, 9H; (CDCl$_3$).

F. To a solution of 9.1 g methyl (5R,6S,8R)-6-(1-trichloroethoxycarbonyloxyethyl)penicillanate in 350 ml distilled methylene chloride at −20° C. under nitrogen is added 62.3 ml of 1 M chlorine/carbon tetrachloride solution. The reaction is stirred for 15 minutes at about −20° C. (until found to be complete by thin layer chromatography eluting with chloroform). The solution is evaporated under vacuum to afford 10.0 g of product comprising (3S,4R,5R)-1-[(2-methyl-1-methoxycarbonyl) prop-1-enyl]-3-(1-trichloroethoxycarbonyloxyethyl)-4-chloroazetidin-2-one.

IR: 1720, 1770–1790 cm$^{-1}$ (chloroform solution)

NMR: δ=5.79–5.81, 1H, d; δ=4.75, 2H, s; δ=3.74, 3H, s; δ=2.27, 3H, s; δ=2.0, 3H, s; δ=1.45–1.54, 3H, d (CDCl$_3$).

G. Through a solution of 7.7 g crude (3S,4R,5R)-1-[2-methyl-1-methoxycarbonyl)prop-1-enyl]-3-(1-trichloroethoxycarbonylosyethyl)-4-chloroazetidin-2-one in 250 ml methylene chloride at about −78° C. with excess ozone. Nitrogen is then bubbled in for 3–5 minutes and then 3 ml dimethylsulfide is added. The solution is allowed to warm to ambient temperature and held for 2 hours. Nitrogen is bubbled through the solution to remove excess dimethylsulfide. Optionally, the solvent may be removed and the residue purified by chromatography to afford (3S,4R,5R)-(2-methoxy-1,2-dioxoethyl)-3-(1-trichloroethoxycarbonyloxyethyl)-4-chloroazetidin-2-one.

NMR: $\delta = 5.97-6.0$, 1H, d; $\delta = 5.76$, 2H, s; $\delta = 4.93$, 2H, s; J=1 c/s, $\delta = 1.45-1.55$, 3H, d.

H. To a solution of 7.8 g potassium hydroxide in 150 ml water and 150 ml. ethanol at 0° C. is added 15.3 ml ethanethiol. After stirring for 10 minutes 38.5 ml carbon disulfide is added. The solution turns deep yellow and is stirred an additional 10 minutes. The solution of paragraph B is cooled to 0° C. and poured into this solution. The mixture is then stirred 45 minutes allowing to warm to ambient temperature. The reaction is followed by thin layer chromatography eluting with chloroform. When the reaction is complete, 200 ml. methylene chloride is added, followed by 20 g citric acid in 200 ml water. The reaction mixture is stirred 5 minutes and then poured into 500 ml methylene chloride. The organic layer is separated, washed first with water, then with cold dilute sodium bicarbonate solution and then again with water. After drying over anhydrous sodium sulfate, the solvent is removed under vacuum. The crude reaction product is chromatographed on coarse silica gel eluting with 20% chloroform/hexane changing to 100% chloroform to afford 6.4 g. (3S,4R,5R)-ethyl [3-(1-trichloroethoxycarbonyloxyethyl)-2-azetidinon-4-yl]-trithiocarbonate, alternatively named as (3S,4R,5R)-3-[1-trichloroethoxycarbonyloxyethyl]-4-[(ethylthio) carbonothioylthio]-azetidin-2-one.

Rotation: $[\alpha]_D^{26} = +154.2°$ (0.4% in dioxane)
NMR: $\delta = 5.6-5.63$, 1H, $\delta = 5.1-5.3$, 1H, m; $\delta = 4.76$, 2H, s; $\delta = 3.17-3.52$. 3H; $\delta = 1.22-1.54$, 6H; (CDCl$_3$).

PREPARATION OF RACEMIC MIXTURES

Example 1 a. Ethyl [1-(Allyloxycarbonylhydroxymethyl)-3-(1-trichloroethoxycarbonyloxyethyl)-2-azetidinon-4-yl]trithiocarbonate (i) Isomer I A mixture of the major isomer of the product thiocarbonate from Preparation F (2.13 g), allyl glyoxylate hydrate (1.0 g) (from Preparation J) and benzene (25 ml) is refluxed under argon with a water collector for 20 hours. The solution is cooled, diluted with dichloromethane (70 ml) and washed with water (2×100 ml), dried and evaporated to give a thin layer chromatography—pure product as a yellow oil.

(ii) Isomer II

Repetition of the procedure of the foregoing paragraph a(i), using the minor isomer of Preparation F (1.02 g) and allyl glyoxylate (0.48 g) in 15 ml benzene with 20 hours reflux is prepared the minor isomer product of this example as a yellow oil.

b. Ethyl [1-(Allyloxycarbonylchloromethyl)-3-(1-trichloroethoxycarbonyloxyethyl)-2-acetidinon-4-yl]trithiocarbonate (i) Isomer I The Isomer I product of the foregoing paragraph a(i) (2.77 g) in dichloromethane (30 ml) and methanesulfonylchloride (0.87 g) is stirred at 0° C., and triethylamine (0.78 g), added dropwise. After 5 minutes at room temperature, the solution is diluted with dichloromethane, washed with 5% aqueous tartaric acid and sodium bicarbonate, dried and evaporated to give a brown oil, having infrared spectrum $\nu_{max}$ (film) at 1770 and 1750–1735 (broad) cm$^{-1}$.

(ii) Isomer I

The procedure of the foregoing paragraph b(i) is followed using the Isomer I product of paragraph a(ii) (1.30 g) in 20 ml dichloromethane with triethylamine (0.29 g) and mesyl chloride (0.33 g). The final solution after workup is filtered through 5 g silica gel, washing with dichloromethane. Evaporation gives the product as a yellow oil (1.0 g), pure by thin layer chromatography with infrared spectrum $\nu_{max}$ (film) 1770, 1755 and 1735 cm$^{-1}$.

c. Ethyl [1-(Allyloxycarbonyl[triphenylphosphoranyl]methyl)-3-(1-trichloroethoxycarbonyloxyethyl)-2-azetidinon-4-yl]trithiocarbonate (i) Isomer I The crude product of the foregoing paragraph b(i) (2.6 g) is stirred with triphenylphosphine (2.8 g) in dry dimethylformamide (30 ml) at room temperature for 40 hours, then extracted with ether, washing with three portions of water. The solution is then dried over anhydrous magnesium sulfate and evaporated. The residue is chromatographed on silica gel (150 g), eluting with 1:1 dichloromethane:hexane to remove excess triphenylphosphine, then with pure dichloromethane to give recovered starting material. The title product is eluted with 5–10% ether-dichloromethane, and pure fractions pooled, evaporated and dried at high vacuum to afford the title compound having infrared spectrum $\nu_{max}$ (CH$_2$Cl$_2$) at 1750, 1730 and 1690 cm$^{-1}$.

(ii) Isomer II

Using 1.08 g of the Isomer II prepared in the foregoing paragraph b(ii) and triphenylphosphine (0.75 g) in dimethylformamide (15 ml) and repeating the procedure of paragraph c(i) with stirring at room temperature for 72 hours affords the desired Isomer I of the title product as a yellow foam.

d. Allyl trans-6-(1-trichloroethoxycarbonylethyl)-2-ethylthiopenem-3-carboxylate (i) Isomer I A solution of the Isomer I phosphorane prepared as in paragraph c(i), (0.975 g) in dry toluene (20 ml) is refluxed under argon in an oil bath at 120°–125° C. for 65 hours, then cooled, diluted with 20 ml hexane and applied to approximately 20 g silica gel. Elution with 1:1 dichloromethane:hexane followed by dichloromethane gives Isomer I of the title compound, which is crystallized from dichloromethane:ether:hexane to give fibrous needles (0.255 g), melting point 123°–127° C. and having infrared spectrum $\nu_{max}$ (CH$_2$Cl$_2$) at 1795, 1745, 1700 cm$^{-1}$.

Anal. Found: C 38.8; H, 3.6; N, 2.9%. C$_{16}$H$_{18}$NO$_6$S$_2$Cl$_3$ req: C 39.15; H, 3.7; N, 2.8%.

(ii) Isomer II

By similar heating of the Isomer II of the phosphorane as prepared in paragraph c(ii) (0.90 g) in toluene (10 ml) for 36 hours and plate chromatography, there is obtained Isomer II of the title product as a yellow oil having infrared spectrum $\nu_{max}$ (CH$_2$Cl$_2$) at 1790, 1750, 1705 cm$^{-1}$.

e. Allyl trans-6-(1-hydroxyethyl)-2-ethylthiopenem-3-carboxylate (i) Isomer I

Isomer I of paragraph d(i) (0.175 g) is stirred at 25° C. for 1 hour with activated zinc dust (0.05 g) in acetic acid (1 ml) and tetrahydrofuran (3 ml). The mixture is diluted with excess dichloromethane and washed with water, aqueous sodium bicarbonate and aqueous sodium chloride, dried and evaporated. The residue is purified on a preparative thin layer chromatography plate eluting with 20% ether-dichloromethane and crystallized from ether-hexane to afford Isomer I of allyl trans-6-(1-hydroxyethyl)-2-ethylthiopenem-3-carboxylate, melting point 65°-66° C. having infrared spectrum $\nu_{max}$ (CH$_2$Cl$_2$) at 3250, 1790 and 1705 cm$^{-1}$.

(ii) Isomer II

In a manner similar to that of paragraph c(i), 0.15 g of Isomer I of paragraph d(i) is deprotected in tetrahydrofuranacetic acid with zinc dust, and chromatographed on a thin layer chromatography plate to obtain Isomer II of allyl trans-6-(1-hydroxyethyl)-2-ethylthiopenem-3-carboxylate, which is crystallized from ether-hexane as cream prisms, melting point 86°-88° C., having infrared spectrum $\nu_{max}$ (CH$_2$Cl$_2$) at 3300, 1795 and 1700 cm$^{-1}$.

Example 2

Repetition of the procedures detailed in paragraphs a through e of Example 1 utilizing the two cis isomers of ethyl [3-(1-trichloroethoxycarbonyloxyethyl)-2-azetidinon-4-yl]trithiocarbonate of Preparation I affords the two cis isomers of allyl cis-6-(1-hydroxyethyl)-2-ethylthiopenem-3-carboxylate.

Example 3

Repetition of the procedures detailed in paragraphs a through e of Example 1 utilizing benzyl [3-(1-trichloroethoxycarbonyloxyethyl)-(2-azetidinon-4-yl)]trithiocarbonate affords the two isomers of allyl trans-6-(1-hydroxyethyl)-2-benzylthiopenem-3-carboxylate.

Example 4

Using 2-trichloroethoxycarbonyloxyethyl-3-(1-trichloroethoxycarbonyloxyethyl)-2-azetidinon-4-yl)trithiocarbonate, the procedure detailed in Example 1 is repeated to obtain the two isomers of allyl trans-6-(1-hydroxy-ethyl)-2-(hydroxyethyl)thiopenem-3-carboxylate.

Example 5

Using methyl [3-(1-trichloroethoxycarbonyloxyethyl)-(2-azetidinon-4-yl)]trithiocarbonate, the procedure detailed in Example 1 is repeated to afford the two isomers of allyl trans-6-(1-hydroxyethyl)-2-methylthiopenem-3-carboxylate.

Example 6

Following the procedure detailed in Example 1 using 3-(1-trichloroethoxycarbonyloxyethyl (2-azetidinon-4-yl)trithiocarbonate there is obtained the two isomers of allyl trans-6-(1-hydroxyethyl)-2-[(2-allyloxycarbonylaminoethyl)thio]penem-3-carboxylate.

Example 7

Repetition of the procedure detailed in Example 1 using n-butyl [3-(1-trichloroethoxycarbonyloxyethyl)-(2-azetidinon-4-yl)]-trithiocarbonate affords the two isomers of allyl trans-6-(1hydroxyethyl)-2-(4-n-butylthio)penem-3-carboxylate.

Example 8

Potassium trans-6-(1-hydroxyethyl)-2-ethylthiopenem-3-carboxylate (i) Isomer I

A solution of Isomer I of allyl trans-6-(1-hydroxyethyl)-2-ethylthiopenem-3-carboxylate (52 mg) and 0.5 m potassium-2-ethylhexanoate (0.36 ml) in 1.2 ml ethyl acetate and 0.8 ml dichloromethane is stirred with addition of 3 mg triphenylphosphine and 5 mg of tetrakis (triphenylphosphine) palladium, under argon. After a few minutes, precipitation of product occurs and after 30 minutes, excess ethyl acetate is added and the precipitate centrifuged. Washing with ether and drying at high vacuum gives, as a yellowish powder, the title product having infrared spectrum $\nu_{max}$ (nujol) at 3300, 1775 and 1600 cm$^{-1}$. By X-ray crystallography of the starting materials the stereochemistry of this compound is designated 5R,6S,8S.

(ii) Isomer II

The procedure of the foregoing paragraph is repeated using Isomer II of allyl trans-6-(1-hydroxyethyl)-2-ethylthiopenem-3-carboxylate (40 mg), 2 ml of 1:1 ethyl acetate:dichloromethane, 0.26 ml of 0.5 m potassium-2-ethylhexanoate, 3 mg triphenylphosphine and 5 mg palladium complex. After 20 minutes, ether (2 ml) is added gradually and the product centrifuged and dried under high vacuum to give the title product as a cream powder having infrared spectrum $\nu_{max}$ (nujol) at 3400, 1780 and 1605 cm$^{-1}$. By X-ray crystallography of the starting materials the stereochemistry of this compound is designated 5R,6S,8R.

Example 9

Repetition of the procedure detailed in Example 8 using the two isomers of allyl cis-6-(1-hydroxymethyl)-2-ethylthiopenem-3-carboxylate affords the two isomers of potassium cis-6-(1-hydroxyethyl)-2-ethylthiopenem-3-carboxylate, i.e., the 5R, 6R, 8R and the 5R, 6R, 8S isomers.

Example 10

Repetition of the procedure detailed in Example 8 utilizing the two isomers of allyl trans-6-(1-hydroxyethyl)-2-benzylthiopenem-3-carboxylate affords potassium (5R,6S,8S)-6-(1-hydroxyethyl)-2-benzylthiopenem-3-carboxylate and the corresponding 5R,6S,8R isomer.

Example 11

Utilization of the two isomers of allyl trans-6-(1-hydroxyethyl)-2-[(2-hydroxyethyl)thio]penem-3-carboxylate in the reaction sequence detailed in Example 8 affords the two isomers (5R, 6S, 8S and 5R, 6S, 8R) of potassium trans-6-(1-hydroxyethyl)-2-[(2-hydroxyethyl)thio]penem-3-carboxylate.

Example 12

Repetition of the procedure detailed in Example 8 using the two isomers of allyl trans-6-(1-hydroxymethyl)-2-methylthiopenem-3-carboxylate affords the two isomers (5R, 6S, 8S and 5R, 6S, 8R) of potassium trans-6-(1-hydroxyethyl)-2-methylthiopenem-3-carboxylate.

Example 13

Each of the two isomers of allyl trans-6-(1-hydroxyethyl)-2[(2-allyloxycarbonylaminoethyl)thio]penem-3-carboxylate (0.04 g) in dichloromethane (0.5 ml) are stirred individually at 25° C. under argon with 2-ethylhexanoic acid (0.04 g), triphenylphosphine (0.007 g) and tetrakis(triphenylphosphine)palladium (0.007 g). After 3 hours, each solid is collected by centrifuge, washed with ethyl acetate and dried at 25° C. in vacuo. Resulting are the two isomers (5R, 6S, 8S and 5R, 6S, 8R) of trans-6-(1-hydroxyethyl)-2-[(2-aminoethyl)thio]penem-3-carboxylic acid.

Example 14

The two isomers of potassium trans-6-(1-hydroxyethyl)-2-ethylthiopenem-3-carboxylate (0.27 g) of Example 8 are individually added to a stirred mixture of dry dimethylformamide (2 ml), pivaloyloxymethyl chloride (0.17 ml) and sodium iodide (0.15 g). The mixture is stirred in the dark under nitrogen for 5 hours, then added to water and extracted with ether. The extract is washed with water, a dilute solution of sodium thiosulfate, and finally with saturated sodium chloride solution, dried and evaporated to obtain the two isomers (5R, 6S, 8S and 5R, 6S, 8R) of pivaloyloxymethyl trans-6-(1-hydroxyethyl)-2-ethylthiopenem-3-carboxylate.

PREPARATION OF OPTICALLY ACTIVE COMPOUNDS

Example 15

A. To a solution of 7.7 g (3S,4R,5R)-3-[1-trichloroethoxycarbonyloxyethyl]-4-[(ethylthio)carbonothioyl-thio]-azetidin-2-one in 90 ml benzene is added 3.5 g allyl glyoxalate. Under nitrogen this mixture is slowly azeotroped for 24 hours. (The reaction is followed by thin layer chromatography eluting with 10% ethyl ether/methylene chloride). Approximately 2.0 ml additional allylglyoxalate is added and the reaction is azeotroped for 10 additional hours. The reaction is then cooled and 150 ml benzene is added. The resultant solution is washed 5 times with 50 ml portions of water. The resultant solution is dried over anhydrous sodium sulfate and the solvents removed under vacuum. Then, 50 ml toluene is added and removed 3 times under high vacuum to afford as the product 9.2 g crude allyl [(3S,4R,5R)-3-(1-trichloroethoxy-carbonyloxyethyl-4-[(ethylthio)carbonothioylthio]-2-azetidinon-1-yl]-2-hydroxyacetate.

Rotation: $[\alpha]_D^{26} = +46.9°$ (0.2% in ethanol)
NMR: $\delta = 6.07-6.21$, 1H; $\delta = 4.76$, 2H, s; $\delta = 3.17-3.52$, 3H; $\delta = 1.22-1.54$, 6H.

B. To a solution of 9.0 g crude allyl [(3S,4R,5R)-3-(1-trichloroethoxycarbonyloxyethyl)-4-[(ethylthio)carbonothioylthio]2-azetidinon-1-yl]-2-hydroxyacetate in 125 ml dry methylene chloride at 0° C. is added 2.8 g methylsulfonyl chloride followed by 2.5 g triethylamine. The reaction is followed by a thin layer chromatography eluting with 5% ethyl ether/methylene chloride. After stirring 45 minutes, 125 ml methylene chloride is added. The reaction is then washed once with cold 10% phosphoric acid solution, once with water, and once with cold dilute sodium bicarbonate solution and then twice with water. The solution is dried over anhydrous sodium sulfate and the solvents are removed under vacuum. The crude product is chromatographed on coarse silica gel with 20% hexane/chloroform to afford 6.9 g allyl [(3S,4R,5R)-3-(1-trichloroethoxycarbonyloxyethyl)-4-[(ethylthio)carbonothioylthio]-2-azetidinon-1-yl]2-chloroacetate.

IR: 1760–1800 cm$^{-1}$ (CDCl$_3$)
NMR: $\delta = 6.23-6.29$, 1H; $\delta = 4.72$, 2H, s; $\delta = 1.24-1.56$, 6H; (CDCl$_3$).

C. To a solution of 6.9 g allyl [(3S,4R,5R)-3-(1-trichloroethoxycarbonyloxyethyl)-4-[(ethylthio)carbonothioylthio]2-azetidinon-1-yl]-2-chloroacetate in 90 ml dimethylformamide at 0° C. is added 4.7 g triphenylphosphine. The reaction is allowed to warm to ambient and is stirred 40 hours. (Completion of reaction is determined by thin layer chromatography eluting with methylene chloride). An additional 780 mg triphenylphosphine is added and the reaction stirred at ambient temperature. After 40 hours, the reaction mixture is poured into 300 ml ethyl ether and washed twice with brine solution and 5 times with water. The solvent is dried over anhydrous sodium sulfate and removed under vacuum. The crude product is chromatographed on coarse silica gel with methylene chloride to afford 6.1 g allyl [(3S,4R,5R)-3-(1-trichloroethoxycarbonyloxyethyl)-4-[(ethylthio)carbonothioylthio]2-azetidinon-1-yl]-2-triphenylphosphine acetate.

Rotation: $[\alpha]_D^{26} = +77.0°$
IR: 1760–1780 cm$^{-1}$ (chloroform solution)
NMR: $\delta = 6.3-6.4$, 1H, $\delta = 4.70$, 2H, s; $\delta = 1.16-1.59$, 6H (CDCl$_3$).

D. A solution of 6.1 g allyl [(3S,4R,5R)-3-(1-trichloroethoxycarbonyloxyethyl)-4-[(ethylthio)carbonothioylthio]-2-azetidinon-1-yl]-2-triphenylphosphine acetate in 400 ml toluene is refluxed under nitrogen for 22 hours. (Reaction is followed by thin layer chromatography eluting with 5% ethyl acetate/toluene.) The toluene is then removed under high vacuum and the reaction mixture is chromatographed on coarse silica gel with toluene, changing to 10% ethyl acetate/toluene. A mixture of 1.5 g reaction product is isolated which rechromatographed and then purified by high pressure liquid chromatography with 2% ethyl acetate/toluene to afford 1.18 g allyl (5R,6S,8R)-2-ethylthio-6-[-1-trichloroethoxycarbonyloxyethyl]penem-3-carboxylate.

Rotation: $[\alpha]_D^{26} = +172.8°$ (0.25% in ethanol).

E. To a solution of 1.18 g allyl (5R,6S,8R)-2-ethylthio-6-[1-trichloroethoxycarbonyloxyethyl]-penem-3-carboxylate in 9.0 ml tetrahydrofuran under nitrogen is added 3 ml acetic acid and 500 mg activated zinc powder. The reaction is stirred for 2½ hours during which time additional 400 mg zinc metal is added in two portions. The reaction is followed by thin layer chromatography eluting with 5% ethyl acetate/toluene. The reaction mixture is then filtered and 150 ml methylene chloride added. After washing twice with water, 3 times with cold 3% sodium bicarbonate solution and twice with brine solution, the solution is dried over anhydrous sodium sulfate. Removal of the solvents under vacuum affords 720 mg allyl (5R,6S,8R)-2-ethylthio-6-(1-hydroxyethyl)penem-3-carboxylate.

F. To a solution of 700 mg allyl (5R,6S,8R)-2-ethylthio-6-(1-hydroxyethyl)penem-3-carboxylate in 4 ml methylene chloride and 8 ml ethyl acetate under nitrogen is added 46.6 mg triphenyl phosphine. To this is added 4.86 ml 0.5 molar potassium-2-ethylhexanoate in ethyl acetate. Then, 51.1 mg tetrakis(triphenylphosphine)palladium is added and the solution is stirred for 15 minutes. An additional 100 mg triphenyl phosphine and 25 mg tetrakis(triphenylphosphine)palladium is added, followed by 10 ml ethyl ether. The product slowly precipitates and after 1 hour the solution is filtered and washed with ethyl acetate and ethyl ether, to afford 45 mg potassium (5R,6S,8R)-2-ethylthio-6-(1-hydroxyethyl)penem-3-carboxylate. To the mother liquor is added 20 ml ethyl ether. After refrigeration overnight, a second crop of crystals is filtered to yield an additional 90 mg of the potassium salt.

NMR: $\delta = 1.25-1.49$, 6H; $\delta = 2.76-3.14$, 2H; $\delta = 3.85-3.94$, 1H; $\delta = 4.12-4.37$, 1H; $\delta = 5.65-5.67$, 1H, d; (D$_2$O)

Rotation: $[\alpha]_D^{26} = -145.2°$

IR: 1600 cm$^{-1}$ and 1770 cm$^{-1}$ (nujol).

Example 16

Alternate Process for the Preparation of Allyl (5R,6S,8R)-6-(1-Trichloroethoxy-Carbonyloxyethyl)-2-Ethylthio-2-penem-3-Carboxylate To a solution of (3S,4R,5R)-3-(1-trichloroethoxy-carbonyloxyethyl)-4-[(ethylthio)-carbonothioylthio]-azetidine-2-one (0.628 g) in methylene chloride (6 ml) cooled to 10° C., add, with stirring, calcium carbonate (0.6 g) followed by allyloxyalyl chloride (0.263 g, 1.2 eq). Add dropwise a solution of di-isopropylethylamine (0.32 ml, 1.2 eq) in methylene chloride (1 ml), during 5 minutes while maintaining the temperature at 10°-15° C. After TLC shows no starting compound (15 minutes) at 15° C., the mixture transfers to a separatory funnel using ethanol-free chloroform. Wash twice with ice/water, filter to remove excess calcium carbonate, dry over anhydrous sodium sulfate, and transfer to a 100 ml 3-neck flask. Adjust the volume of the solution to approximately 50 ml with chloroform and heat at reflux temperature while adding a solution of triethylphosphite (0.6 ml, 2 eq) in chloroform (20 ml) over a 3 hour period. Reflux the mixture for an additional 18 hours, evaporate and chromatograph on 14 g silica gel, eluting with 25% ether-hexane, and evaporating the combined like elutes to obtain a residue (420 mg) comprising the title compound (58% yield). Purify by crystallization from ether-hexane to obtain the title compound in crystalline form. Yield 330 mg (46% theory). Remove the trichlorothoxycarbonyl-protecting group in the manner described in Example 15E and the allyl ester in the manner described in Example 15F to obtain potassium (5R,6S,8R)-2-ethylthio-6-(1-hydroxyethyl)penem-3-carboxylate.

The following formulations are to exemplify some of the dosage forms in which the antibacterial agents of this invention may be employed. In each, the active ingredient is designated by the term "Drug" which is meant to indicate one of the following compounds: potassium (5R,6S,8R)-6-(1-hydroxyethyl)-2-ethylthiopenem-3-carboxylate, potassium (5R,6S,8R)-6-(1-hydroxyethyl)-2-methylthiopenem-3-carboxylate, and (5R,6S,8R)-6-(1-hydroxyethyl)-2-ethylthiopenem-3-carboxylic acid. It will be appreciated, however, that each of these compounds may be replaced by equally effective quantities of other compounds defined by formula I.

Example 17

Injection Formulation

Per vial: potassium (5R,6S,8R)-6-(1-hydroxyethyl)-2-ethylthiopenem-3-carboxylate (Sterile powder)

Add sterile water for injection U.S.P. or bacteriostatic water for injection U.S.P., for reconstitution.

Example 18

| Injectable Suspension Formulation | mg/ml |
|---|---|
| Sterile drug | 250.0 |
| Benzyl Alcohol | 9.0 |
| Methylparaben | 1.8 |
| Propylparaben | 0.2 |
| Sodium Carboxymethylcellulose | 5.0 |
| Polyethylene Glycol 4000 | 10.0 |
| Povidone | 5.0 |
| Sodium Citrate | 15.0 |
| Disodium Edetate | 0.1 |
| Water for Injection | q.s. |
| To make | 1.0 ml |

Dissolve parabens in a portion of the water for injection by heating it to 65°-70° C. Cool to 25°-35° C. Charge and dissolve benzyl alcohol, sodium citrate, disodium edetate, PEG 4000, povidone and sodium carboxymethylcellulose. Filter the solution and sterilize by autoclaving. Make a slurry of the sterile active and pass it through a colloid mill. Mix it well with solution from Step 3 and pass it through the mill. Bring the suspension to the final volume/weight and fill into sterile containers.

Example 19

| | Capsule Formulation | | |
|---|---|---|---|
| Item No. | Ingredient | mg/capsule | mg/capsule |
| 1 | Drug | 250 | 500 |
| 2 | Lactose, USP | 106 | 123 |
| 3 | Corn Starch, Food Grade | 40 | 70 |
| 4 | Magnesium Stearate, USP | 4 | 7 |
| | | 400 mg | 700 mg |

Mix Item Nos. 1, 2 and 3 in a suitable mixer for 10-15 minutes. Add Item No. 4 and mix for 1-3 minutes. Fill the above mixture into suitable 2-piece hard gelatin capsules.

Example 20

| | Tablet Formulation | | |
|---|---|---|---|
| Item No. | Ingredient | mg/tablet | mg/tablet |
| 1 | Drug | 250 | 500 |
| 2 | Lactose, USP | 106 | 112 |
| 3 | Corn starch, Food Guide as 10% paste in water | 20 | 40 |
| 4 | Corn starch, Food Guide | 20 | 40 |
| 5 | Magnesium Stearate | 4 | 8 |
| | | 400.0 mg | 800.0 mg |

Mix Item Nos. 1 and 2 in a suitable mixer for 10-15 minutes. Granulate the mixture with Item No. 3. Pass the wet granulation through a coarse screen ($\frac{1}{4}"$). Dry the wet granules for 8-12 hours at 40°-50° C. Using a suitable mill, pass the dried granules through a medium screen (No. 12 to No. 16). Add Item No. 4 and mix for 10-15 minutes. Add Item No. 5 and mix further for 1-3 minutes. Compress the mixture to appropriate size and weight on a suitable tablet machine.

Example 21

| Cream Formulations | mg/g |
|---|---|
| A. | |
| Drug | 1.0 |
| Cetyl Esters Wax | 20.0 |
| Cetyl Stearyl Alcohol | 100.0 |
| Sorbitan Monostearate | 25.0 |
| Polysorbate 60 | 20.0 |
| Cetyl Dodecanal | 100.0 |
| Propylene Glycol | 100.0 |
| Benzyl Alcohol | 10.0 |
| Purified Water      To make | 1 g |
| B. | |
| Drug | 10.0 |
| Stearic Acid | 60.0 |
| Propylene Glycol Monostearate | 100.0 |
| Isopropyl Myristate | 50.0 |
| Propylene Glycol | 100.0 |
| Polyoxyethylene 20 Sorbitan Monopalmitate | 60.0 |
| Methylparaben | 1.0 |
| Butylparaben | 4.0 |
| Purified Water      To make | 1 g |

Example 22

| Gel Formulations | mg/g |
|---|---|
| A. Drug | 5.0 |
| Propylene Glycol | 50.0 |
| Hydroxypropyl Cellulose | 20.0 |
| Alcohol      To make | 1 g |
| B. Drug | 2.5 |
| Propylene Glycol | 350.0 |
| Alcohol | 350.0 |
| Carbomer 940 | 20.0 |
| Monoamylamine | 2.0 |
| Purified Water      To make | 1 g |

Example 23

| Solution Formulations | |
|---|---|
| A. Drug | 7.5 |
| Isopropanol | 700.0 |
| Purified Water      To make | 1 g |
| B. Drug | 2.0 |
| Acetone | 100.0 |
| Isopropyl Myristate | 50.0 |
| Alcohol      To make | 1 g |

Example 24

| Aerosol Formulation | |
|---|---|
| Drug | 10.0 |
| PPG-12-Buteth-16 | 50.0 |
| Alcohol | 150.0 |
| Hydrocarbon Propellant      To make | 1 g |

Example 25

| Lotion Formulation | |
|---|---|
| Drug | 5.0 |
| Ethyl Alcohol | 400.0 |
| Polyethylene Glycol 400 | 300.0 |
| Hydroxypropyl Cellulose | 5.0 |
| Propylene Glycol      To make | 1 g |

Example 26

| Pump Spray Formulation | |
|---|---|
| Drug | 10.0 |
| Isopropyl Alcohol | 400.0 |
| Purified Water      To make | 1 g |

Example 27

| Oral Suspension | |
|---|---|
| Drug | 100.0 |
| Microcrystalline Cellulose | 15.0 |
| Flavor(s)   q.s. | |
| Sugar | 300.0 |
| Purified Water   q.s.   ad | 1000.0 |

Example 28

| Oral Solution | |
|---|---|
| Drug | 250.0 |
| Propylene Glycol | 50.0 |
| Alcohol | 50.0 |
| Sorbitol Solution | 200.0 |
| Sugar | 550.0 |
| Flavor   q.s. | |
| Color   q.s. | |
| Purified Water   q.s.   ad | 1000.0 |

What is claimed is:

1. A compound of the formula:

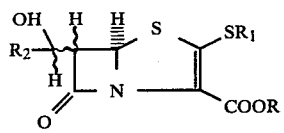

wherein R is hydrogen, an alkali metal cation, a metabolisable ester group; $R_1$ is lower alkyl, lower alkyl substituted by one or more phenyl groups, amino(lower)alkyl, mono- or di-(lower)alkylamino(lower)alkyl, carboxy(lower)alkyl, loweralkylcarbonylamino(lower)alkyl, halo(lower)alkylcarbonylamino(lower)alkyl, hydroxy(lower)alkyl, hydroxyaralkyl wherein the aralkyl moiety is a lower alkyl substituted by one or more phenyl groups, alkoxycarbonyl(lower)alkyl, or lower alkyl substituted with an unsubstituted or a lower alkyl substituted aromatic heterocyclic group having at least one nitrogen, oxygen or sulfur ring heteroatom; and $R_2$ is phenyl or substituted phenyl wherein said substituents are one or more of lower alkyl, lower alkoxy, or halogen, lower alkyl substituted by one or more phenyl groups, an unsubstituted or substituted aromatic heterocyclic group having at least one nitrogen, oxygen or sulfur heteroatom wherein said substituents are from 1 to 3 lower alkyl groups, lower alkyl substituted with an unsubstituted or a lower alkyl substituted aromatic heterocyclic group having at least one nitrogen, oxygen or sulfur ring heteroatom or hydroxyaralkyl wherein the aralkyl moiety is a lower alkyl substituted by one or more phenyl groups; and the pharmaceutically acceptable salts thereof.

2. A compound according to claim 1 wherein $R_1$ is lower alkyl.

3. A compound according to claim 2 wherein the stereochemistry is 5R,6S,8R when $R_2$ is lower alkyl substituted by one or more phenyl groups, lower alkyl substituted with an unsubstituted or a lower alkyl substituted aromatic heterocyclic group having at least one nitrogen, oxygen or sulfur ring heteroatom or hydroxyaralkyl wherein the aralkyl moiety is a lower alkyl substituted by one or more phenyl groups and is 5R,6S,8S when $R_2$ is phenyl or substituted phenyl wherein said substituents are one or more of lower alkyl, lower alkoxy or halogen or an unsubstituted or substituted aromatic heterocyclic group having at least one nitrogen, oxygen or sulfur heteroatom wherein said substituents are from 1 to 3 lower alkyl groups.

4. A compound according to claim 3 which is (5R,6S,8S)-6-(2-hydroxybenzyl)-2-loweralkylthiopenem-3-carboxylate and alkali metal salts thereof, said lower alkyl having 1 to 3 carbon atoms.

5. A compound according to claim 4 wherein said lower alkyl is methyl.

6. A compound according to claim 4 wherein said lower alkyl is propyl.

7. The compound according to claim 3 which is potassium (5R,6S,8S)-6-[1-hydroxy-1-(4-pyridyl)methyl]-2-methylthiopenem-3-carboxylate.

8. The compound according to claim 3 which is potassium (5R,6S,8S)-6-(α-hydroxy-p-hydroxybenzyl)-2-methylthiopenem-3-carboxylate.

9. The compound according to claim 3 which is potassium (5R,6S,8S)-6-(α-hydroxy-p-methylbenzyl)-2-ethylthiopenem-3-carboxylate.

10. The compound according to claim 3 which is (5R,6S,8S)-6-[1-hydroxy-1-(2-thienyl)methyl]penem-3-carboxylic acid.

11. The compound according to claim 3 which is potassium (5R,6S,8R-6-(α-hydroxyphenethyl)-2-methylthiopenem-3-carboxylate.

12. A compound according to claim 1 wherein $R_1$ is amino(lower)alkyl.

13. A compound according to claim 12 wherein the sterochemistry is 5R,6S,8R when $R_2$ is lower alkyl substituted by one or more phenyl groups, lower alkyl substituted with an unsubstituted or a lower alkyl substituted aromatic heterocyclic group having at least one nitrogen, oxygen or sulfur ring heteroatom or hydroxyaralkyl wherein the aralkyl moiety is a lower alkyl substituted by one or more phenyl groups and is 5R,6S,8S when $R_2$ is phenyl or substituted phenyl wherein said substituents are one or more of lower alkyl, lower alkoxy or halogen or an unsubstituted or substituted aromatic heterocyclic group having at least one nitrogen, oxygen or sulfur heteroatom wherein said substituents are from 1 to 3 lower alkyl groups.

14. The compound according to claim 13 which is (5R,6S,8S)-6-(α-hydroxybenzyl)-2-(2-aminoethylthio)-penem-3-carboxylic acid.

15. A pharmaceutical composition comprising an antibacterially effective amount of a compound of claim 1 together with a non-toxic pharmaceutically acceptable carrier.

16. A method of eliciting an antibacterial response in a warm-blooded animal having a susceptible bacterial infection which comprises administering to said animal a non-toxic, antibacterially effective amount of a compound of claim 1.

* * * * *